United States Patent [19]

Sandridge

[11] Patent Number: 5,299,575
[45] Date of Patent: Apr. 5, 1994

[54] SHORT EXCHANGE GUIDING CATHETER APPARATUS AND METHOD

[76] Inventor: James B. Sandridge, 2044 Eagle Nest, Lewisville, Tex. 75067

[21] Appl. No.: 919,048

[22] Filed: Jul. 23, 1992

[51] Int. Cl.$^5$ .............................................. A61B 6/00
[52] U.S. Cl. ...................................... 128/658; 604/96; 606/194
[58] Field of Search ..................... 128/656–658, 128/772; 604/96, 165; 606/194

[56] References Cited

U.S. PATENT DOCUMENTS

| | | | |
|---|---|---|---|
| 4,089,337 | 5/1978 | Kronner | 128/656 |
| 4,150,676 | 4/1979 | Jackson | 128/657 |
| 4,176,662 | 12/1979 | Frazer | 128/657 |
| 4,545,390 | 10/1985 | Leary | 128/657 |
| 4,589,410 | 5/1986 | Miller | 128/657 |
| 4,932,959 | 6/1990 | Horzewski et al. | 606/194 |
| 5,054,500 | 10/1991 | Littleford et al. | 128/772 |
| 5,059,178 | 10/1991 | Ya | 604/101 |
| 5,105,812 | 4/1992 | Corman | 604/96 |

Primary Examiner—Max Hindenburg
Attorney, Agent, or Firm—Hubbard, Tucker & Harris

[57] ABSTRACT

A guiding catheter used for coronary angioplasty procedures includes an inflatable bag on the inner wall of the guiding catheter. The guiding catheter directs a guide wire for a balloon catheter to a coronary artery for opening a blockage in the artery. When the inflatable bag is inflated it pinches the guide wire against the inner wall of the guiding catheter. This procedure enables the guide wire to be secured in or near a coronary artery while the balloon catheter is exchanged. A hypotube runs along the inner wall of the guiding catheter from an inflation syringe near the catheter hub to the inflatable bag. Preferably saline solution is injected into the inflatable bag.

10 Claims, 3 Drawing Sheets

SHORT EXCHANGE GUIDING CATHETER APPARATUS AND METHOD

BACKGROUND OF INVENTION

The present invention relates to a guiding catheter used in Percutaneous Transluminal Coronary Angioplasty procedures. More particularly, the present invention concerns a guiding catheter having an inflatable balloon disposed in its wall for securing a guide wire within the lumen of the guide catheter during replacement of a balloon catheter on the guide wire.

In Percutaneous Transluminal Coronary Angioplasty (PTCA) procedures, a balloon catheter is introduced into an artery for the purposes of enlarging a vessel or opening a clogged artery or stuck valve in the heart or elsewhere to restore normal blood flow. A peripheral introduction of a balloon tip catheter enlarges and dilates a narrowed arterial lumen by inflating the catheter tip.

During PTCA it may be necessary to remove a balloon catheter from the guide wire in the guide catheter. Three common situations occur in which a balloon catheter is exchanged. One is when the first balloon does not satisfactorily reduce the transtenotic gradient and a high degree of residual stenosis exists. The balloon catheter is usually removed and a larger balloon inserted to complete the dilation.

Another situation arises when the lesion is too tight to accommodate the balloon. Here the balloon needs to be removed and replaced with a smaller balloon catheter to partially dilate the lesion, and the larger balloon reinserted to complete the dilation. In the third case, the operator may wish to inject a large volume of contrast to achieve maximum visualization of the lesion. This is accomplished by pulling the balloon into the catheter body before injecting the contrast. The position of the guide wire must be maintained across the lesion so that the balloon catheter may be repositioned if needed.

To facilitate a catheter balloon exchange, it is common to use a guide wire that is twice as long as the steerable guide wire to pull the balloon dilation catheter back without removing the guide wire. Otherwise when a catheter wire is removed, replacement of the wire will require renegotiation of the anatomy with a new wire, increasing the risks of intimal dissection. Conventional devices employ an exchange-wire technique to achieve the extra length. A crimping tool is used to bond an extension wire to the catheter wire so that the balloon catheter can be exchanged without removing the wire. However, users frequently encounter problems when sliding the catheter balloon over the crimped portion of the wire.

Other devices employ an extra guide wire during the entire procedure. In both techniques the process is cumbersome, requiring several additional steps, increasing fluoroscopy time, and increasing the risk of losing the position of the guide wire. Another device, called a trapper, incorporates a balloon that is separately inserted into the guiding catheter to trap the guide wire against the catheter wall. Use of the trapper device is cumbersome because it is separate from the catheter, involves additional hardware and requires an involved procedure.

Further details of the devices used in angioplasty procedures can be found in U.S. Pat. No. 4,932,959 (Horzewski), U.S. Pat. No. 5,054,500 (Littleford) and U.S. Pat. No. 5,059,178 (Ya). U.S. Pat. No. 4,932,959 (Horzewski) discloses a dilation catheter with a releasably secured guide wire. The apparatus discloses inner and outer tubular members that are concentrically disposed. The inner tubular member incorporates a flexible portion therein. An annular passageway is defined between the two tubular members, which contains inflation fluids. When inflation fluid is directed into the annular passageway, the flexible portion of the inner tubular member expands inwardly to grip the guide wire disposed within the inner lumen thereof to improve the pushability of the moveable catheter assembly.

U.S. Pat. No. 5,054,500 (Littleford) relates to an apparatus and method for guiding and positioning a catheter. The apparatus incorporates an inflatable outer collar at the distal end of the catheter body for controlling the position of the catheter, which may be inflated to press against the passageway to hold the guide catheter in place during operation.

U.S. Pat. No. 5,059,178 (Ya) discloses a method of isolating a thrombus in the blood vessel of a patient. The catheter apparatus discloses a first and second inflatable balloon. The first balloon is positioned downstream of the thrombus, and the second balloon is positioned upstream of the thrombus. The purpose of the balloons is to isolate the thrombus so that a thrombus dissolving agent may be applied in isolation from the rest of the body. Once the thrombus is dissolved, it is removed through a suction catheter. A third balloon is disclosed, which is used to expand the stricter after the thrombus is removed.

None of the foregoing patents disclose a satisfactory means for retaining a guide wire in position during the exchange of balloon catheters. A need exists for a more efficient apparatus and method for exchanging balloon catheters without the risks and complicated procedures associated with the prior art.

SUMMARY OF THE INVENTION

The present invention provides for a guiding catheter including a tubular member having a means to perform the angioplasty treatment of a vessel and a catheter hub. The tubular member incorporates a securing balloon in the lumen of the tubular body of the guiding catheter. The securing balloon communicates with a hypotube, which forms a second lumen, through an aperture that extends from the first lumen into the wall of the catheter body. The hypotube is disposed in or along the wall of the catheter body and extends from the securing balloon to an aperture in a catheter hub.

A medium is introduced through the aperture in the catheter hub for inflating the securing balloon. When the securing balloon is deflated, it lies flat against the inner surface of the catheter body. If a balloon catheter exchange is needed, the catheter balloon is pulled back into the catheter guide, and the securing balloon is inflated by a medium, which is introduced into the hypotube. When fully inflated, the securing balloon expands into the lumen of the catheter body until it presses the guide wire against the inner surface of the guide catheter tube, thereby fixing the position guide wire during an exchange of a balloon catheter.

DETAILED DESCRIPTION OF THE PREFERRED EMBODIMENTS

Figure 1:
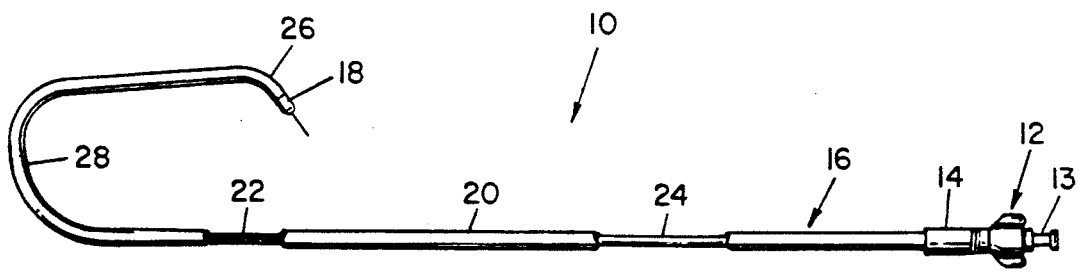
FIG. 1 is a diagrammatic view of a prior art guiding catheter.

Referring first to FIG. 1, a typical prior art guiding catheter 10 is shown. The catheter includes a hub section 12 with a luer 13, a strain relief section 14, a extended shaft 16 and a tip 18. The shaft 16 usually includes an outer jacket 20 made of a plastic, such as polyurethane, which provides both support and memory so as to maintain curvature. Beneath the outer jacket is a wire braid 22 which provides torque control and an inner lining 24 made of a low friction materials, such as Teflon, which decreases the friction coefficient between the guide catheter inner wall and the balloon catheter. Guide catheters have certain design differences depending upon whether they are used to access the aorta through the femoral artery (thigh) or brachial artery (upper arm). Thermal plastics may be used in the outer layer 20 in order to enhance the support memory so as to maintain primary curves 26 and secondary curves 28.

Figure 2:
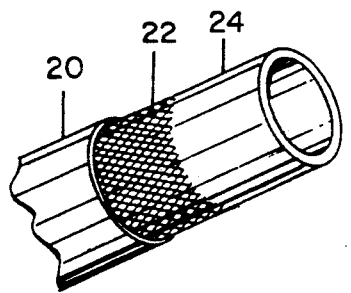
FIG. 2 is a partial cutaway view of the tube wall of the guiding catheter of FIG. 1.
Figure 3:
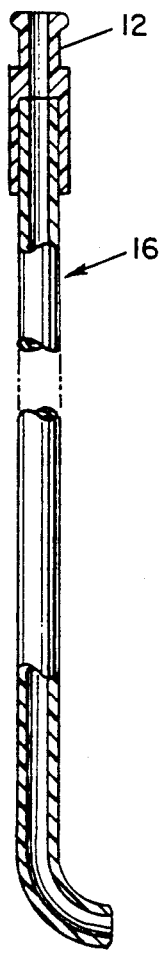
FIG. 3 is a diagrammatic view of a simplified partial cross section of a prior art guiding catheter.

Looking now at FIG. 3, a cross-section is shown of a typical prior art guiding catheter assembly 10 such as that shown in FIG. 1. Hub section 12 typically has the end of extended shaft 16 embedded therein. The walls of shaft 16 extend uniformly from hub 12 to the end of the assembly. As previously discussed, the walls of the shaft include an outer jacket 20, a inner wire braid lining 22 and a internal hollow core 24 made of a low friction material such Teflon, as best shown in FIG. 2.

Figure 4:
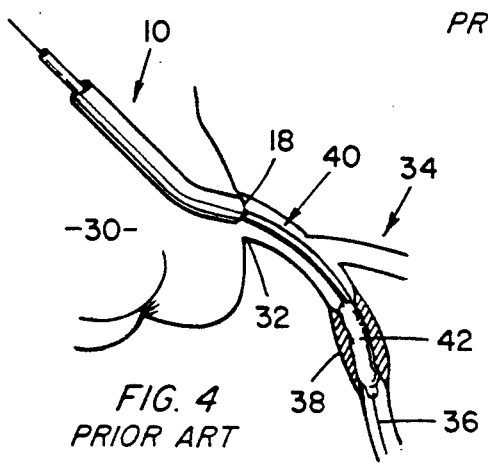
FIG. 4 is a diagrammatic view of a PTCA procedure using the prior art guiding catheter of FIG. 1.

FIG. 4 shows the prior art catheter 10 of FIG. 1 in use in a typical PTCA procedure. In order to access the blood vessels of the heart, the typical PTCA procedure begins with the insertion of guide catheter 10 into the femoral or brachial artery. From there the guide catheter is manipulated into the aorta which terminates at the aortic root 30. The right and left coronary arteries open from the aortic root to provide blood flow passageways for the heart.

As shown in FIG. 4, the tip 18 of catheter 10 is inserted through the aortic root to the opening (ostium) 32 of the left coronary artery (LCA) 34. A guide wire 36 is then directed into luer 13 at hub 12 of catheter 10 (see FIG. 1). The guide wire travels through guide catheter 10 and into left coronary artery 34 to a point past a lesion 38 which is partially blocking artery 34.

Next a balloon catheter 40 is threaded onto guide wire 36 and slipped along guide wire 36 to artery 34. The balloon catheter includes a balloon tip 42 which is extended to the position of lesion 38 where it is expanded to open the lesion and improve blood circulation.

During the course of the angioplasty procedure, it may be necessary to remove the balloon catheter 40 and insert a larger or smaller one. This procedure is difficult if not impossible with a standard length guide wire (about 180 cm long) without also withdrawing the guide wire, a highly undesirable consequence. The prior art alternatives are to utilize a much longer guide wire (about 300 cm long) or to crimp on an extension wire to extend the length. As discussed above, both procedures are cumbersome and difficult. The present invention provides an apparatus and procedure to hold the guide wire 36 in place during balloon catheter exchange.

Figure 5:
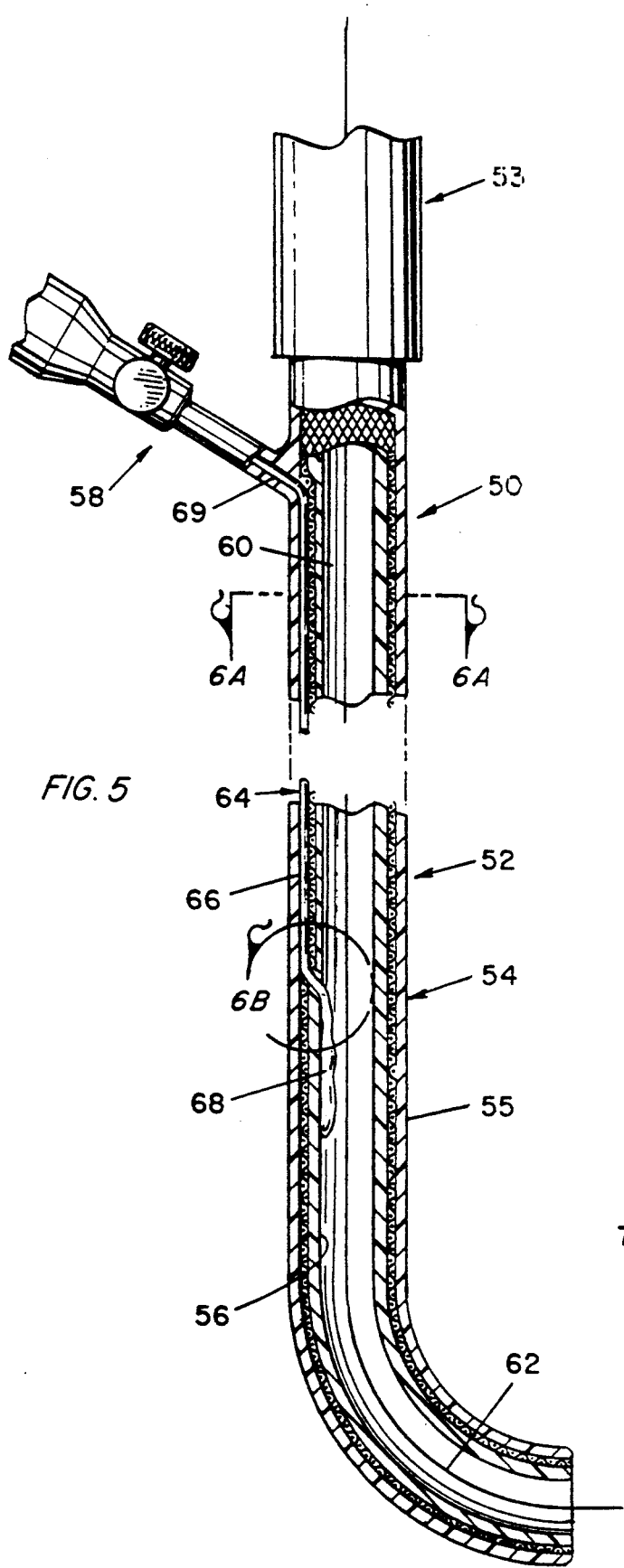
FIG. 5 is a diagrammatic view of a partial cross-section of the short exchange guiding catheter assembly of the present invention.

Looking now at FIG. 5, a preferred embodiment of the short exchange guiding catheter assembly 50 according to the present invention is shown. Assembly 50 includes a catheter body 52 and catheter hub 53. Catheter body 52 is formed by a long narrow tube 54, preferably cylindrical in shape, with a outer surface 55 and an inner surface 56. Preferably tube 54 is constructed of a conventional flexible material of the type described above with respect to conventional guiding catheters. Catheter hub 53 is a conventional unit in most respects, similar to hub 12 in FIG. 1.

Exchange catheter tube 54 has a first lumen (passageway) 60 within tubular member body 52 through which a guide wire 62 is slidably disposed, in a conventional manner. A second smaller lumen 64 is formed by an inner passageway in one side of tube 54 having a hypotube 66 encapsulated therein. The distal end of the hypotube 66 terminates in a balloon 68 formed in the wall of tube 54. The proximal portion of hypotube 66 opens into a passageway 69 within catheter wall 54 which connects to a syringe 58.

Figure 6A:
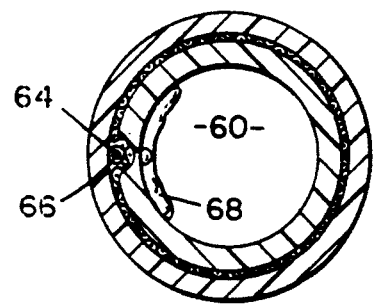
FIG. 6A is a cross-sectional view taken across line 6A—6A in FIG. 5.
Figure 6B:
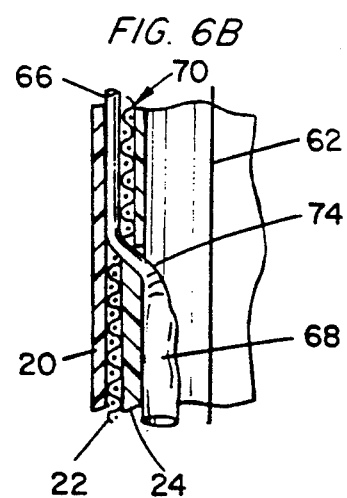
FIG. 6B is a blown-up view at Circle 6B of the partial cross-section view of FIG. 5.

Looking at FIG. 6A, the small lumen 64 formed by hypotube 66 in the wall of guiding catheter tube 54 is shown. The securing balloon 68 is located in lumen 60 at the distal end of hypotube 66. The manner in which hypotube 66 is disposed within the wall 54 of guiding tube 52 is somewhat discretionary. As shown in FIGS. 6A and 6B, the wall 54 of guiding catheter tube 52 includes a teflon core 24, an inner wire braid jacket 22 and an outer plastic jacket 20, preferably made of urethane. Core 24 is hollow providing for an inner lumen 60 which serves as a guide shaft for the guide catheter assembly 10.

In FIG. 6B, a blown up view of the guide catheter tube wall is shown in which a portion of the inner core 24 is removed or tapered to form a channel 70 within which the hypotube 66 is laid. Preferably the wire braid 22 also lies within channel 70 with the hypotube 66 disposed thereon. Outer jacket 20 remains circular in form providing the channel opening 70 between jacket 20 and wire braid cover 22.

Figure 6C:
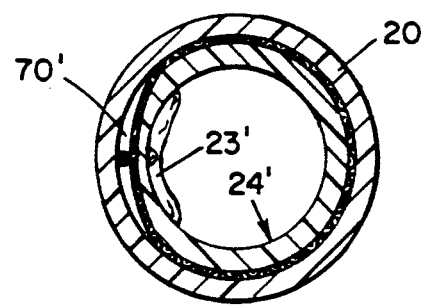
FIG. 6C is a cross-sectional view corresponding to FIG. 6A of an alternate preferred embodiment of the invention.

Channel 70 is preferably formed by removing a portion of inner core 24 from the catheter hub point to the location of the catheter where the balloon 68 is disposed, as shown in FIG. 6B. At that point, a passageway 74 extends through the wire braid 22 and teflon core 24 to communicate between hypotube 66 and inflation bag 68 which is deflated and lies within inner lumen 60. Alternately, as shown in FIG. 6C, channel 70' may be formed by providing an irregular shaped inner core 24' in which a portion 23' of the circumference is restricted slightly to leave a pocket 70' or channel between that portion and the outer jacket 20.

Figure 7:
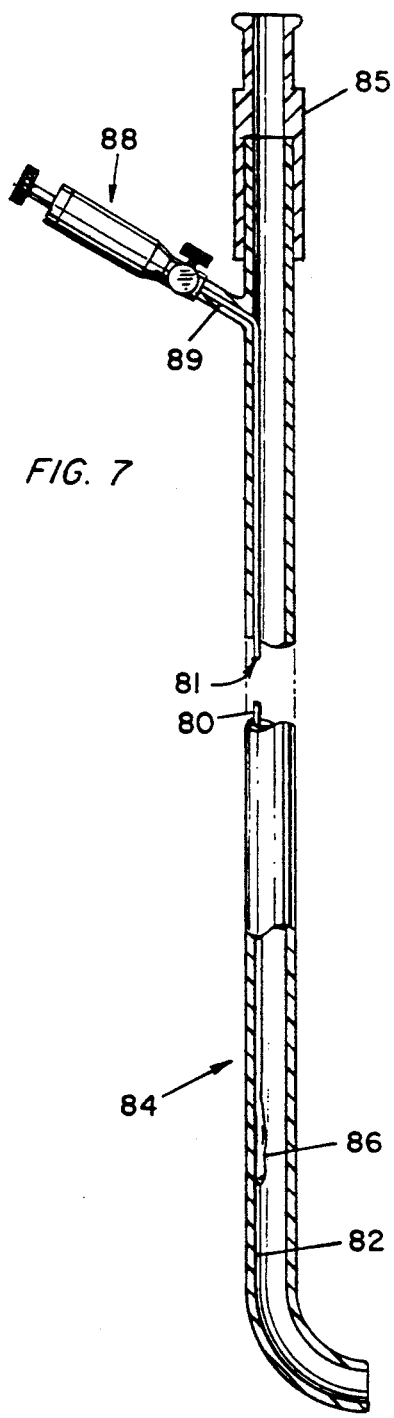
FIG. 7 is a cross-sectional view of a guiding catheter assembly in accordance with another preferred embodiment of the present invention.

Another preferred embodiment is shown in FIG. 7 in which a hypotube 80 extends along the inside of inner wall 82 of guiding catheter shaft 84 to form a small lumen 81. Hypotube 80 terminates in inflatable balloon 86 which also lies along the inner wall 82 of catheter shaft 84. Hypotube 80 and balloon 86 may be affixed to the inside of catheter wall 82 by any conventional adhesive or other proper means for attachment. A syringe 88 extends through an opening 89 in catheter wall 84 to communicate with the lumen 81 formed by hypotube 80.

Figure 8:
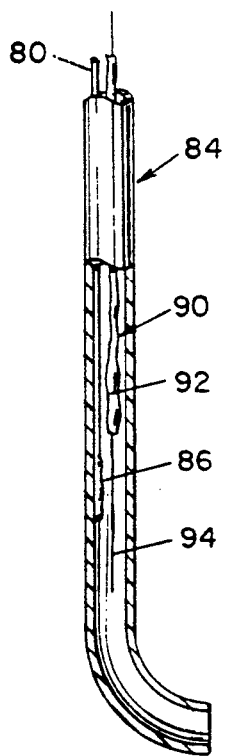
FIG. 8 is a schematic view of the guiding catheter assembly shown in FIG. 7 with the securing balloon in a deflated position.

Referring now to FIG. 8, the operation of the short exchange guide catheter 84 of FIG. 7 is shown. As discussed earlier, a balloon catheter 90 having a balloon tip 92 is threaded onto guide wire 94. When an exchange of the balloon catheter is required, catheter 90 is retracted on guide wire 94 into guide catheter 84 to a point proximal of securing balloon 86. Normally there is enough spare guide wire for this retraction without causing the balloon catheter to slip off of the guide wire at hub 85.

Figure 9:
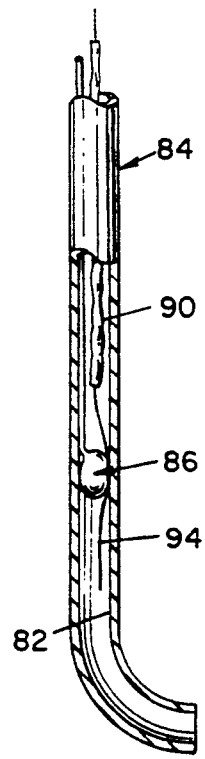
FIG. 9 is a schematic view of the guiding catheter assembly shown in FIG. 7 with the securing balloon in an inflated position.

As shown in FIG. 9, securing balloon 86 is then inflated by the injection of an innocuous solution such as saline from syringe 88 through lumen 81. As securing balloon 86 inflates, guide wire 94 is pinned against the inner wall 82 of guiding catheter 84. With guide wire 94 securely in place, balloon catheter 90 may be removed and replaced without disturbing the guide wire position.

Figure 10:
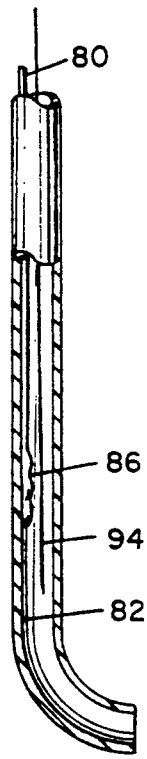
FIG. 10 is a schematic view of the guiding catheter assembly shown in FIG. 7 with the securing balloon deflated and the balloon catheter withdrawn.

As shown in FIG. 10, after the balloon catheter 90 is exchanged, syringe 88 is operated to remove the inflation medium from securing balloon 86, thus releasing guide wire 94 from its fixed position. Preferably, balloon 86 is fully deflated so that it rests approximately flat against the inner surface 82 of guide catheter tube 84 when not in use.

Preferably, hypotube 80 is a hollow metal tube such as stainless steel and securing balloon 86 is made out of latex so as to provide strength and flexibility. Syringe 88 is preferably a conventional syringe of a type which can easily inflate and deflate balloon 86 through small lumen 81. The other materials of guiding catheter 84 in accordance with the present invention are normal conventional materials.

A typical outer diameter of catheter tube 84 is approximately 0.104". The conventional inner diameter of a guiding catheter is usually about 0.084". In the present invention, it is expected that the inner diameter of the main lumen is 0.079", leaving a wall thickness of 0.025". The diameter of the small lumen 81 is preferably 0.015". The inflation diameter of securing balloon 86 is preferably at least 0.084" so as to securely pin the guide wire against the inner wall 82 of the guide catheter tube 84.

Although the foregoing description shows a preferred embodiment of the present invention, it is understood that other obvious modifications or changes may be made within the scope of the present invention. Accordingly, the present invention is intended to encompass such changes and modifications which fall within the intent and scope of the invention.

What is claimed is:
1. A short exchange guiding catheter, comprising:
 (a) a guide catheter hub,
 (b) an elongated guide catheter connected to the guide hub and forming a guide lumen therein for directing a guide wire extending from the hub through the guide lumen,
 (c) a hypotube running along the guide catheter substantially the length of the guide catheter and forming an inflation lumen,
 (d) an inflatable balloon within the guide lumen in communication with the inflation lumen, and
 (e) inflation means in communication with the inflation lumen for inflating and deflating the balloon.

2. The catheter of claim 1 wherein the inflation balloon is secured along the inner wall of the guide lumen near the end of the guide catheter.

3. The catheter of claim 1 wherein the hypotube is imbedded with the wall of the guide catheter.

4. The catheter of claim 1 wherein the hypotube is secured to the inner wall of the guide lumen.

5. The catheter of claim 1 wherein the guide catheter has an inner core and an outer jacket.

6. The catheter of claim 5 wherein the circumference of the inner core is irregular to form a passageway for the hypotube.

7. The catheter of claim 5 wherein the inner core is channeled to form a passageway for the hypotube.

8. A short exchange guiding catheter for use in exchanging a balloon catheter over a guide wire while securing the guide wire within a lumen of the guiding catheter, comprising:
 a tubular member including a hollow inner core forming a guide lumen therein through which the guide wire may be passed, the inner core having an irregular circumference substantially the length of the guiding catheter;
 a hypotube disposed longitudinally adjacent the irregular circumference of the inner core substantially the length of guiding catheter;
 inflatable means at the distal end of the hypotube; and
 inflation means associated with the tubular member and in communication with the hypotube to inflate the inflatable means.

9. A short exchange guiding catheter for use in exchanging a balloon catheter over a guide wire while securing the guide wire within a lumen of the guiding catheter, comprising:
 a tubular member including a hollow inner core forming a guide lumen therein through which the guide wire may be passed, the inner core having a longitudinal channel running substantially the length of the guiding catheter;
 a hypotube disposed in the channel of the inner core substantially the length of the channel;
 inflatable means at the distal end of the hypotube; and
 inflation means associated with the tubular member and in communication with the hypotube to inflate the inflatable means.

10. A short exchange guiding catheter for use in exchanging a balloon catheter over a guide wire while securing the guide wire within a lumen of the guiding catheter, comprising:

a hollow tubular member forming a guide lumen therein through which the guide wire may be passed;

a passageway formed in a channel within the wall of the tubular member, the passageway running along the tubular member substantially the length of the guiding catheter;

inflatable means affixed to the inner wall of the tubular member at the distal end of the passageway, the inflatable means communicating with the passageway by an outlet running through the inner wall between the passageway and the inflatable means; and inflation means associated with the tubular member and in communication with the passageway to inflate the inflatable means.

* * * * *